(12) United States Patent
Zeltner

(10) Patent No.: US 7,166,091 B1
(45) Date of Patent: Jan. 23, 2007

(54) RECREATIONAL BELT FOR SUPPORTING AND HOUSING AN OSTOMY APPLIANCE

(76) Inventor: Keith Zeltner, 6th N. York Rd. 2nd Floor, Hatboro, PA (US) 19040

( * ) Notice: Subject to any disclaimer, the term of this patent is extended or adjusted under 35 U.S.C. 154(b) by 32 days.

(21) Appl. No.: 11/006,241

(22) Filed: Dec. 7, 2004

Related U.S. Application Data

(60) Provisional application No. 60/528,945, filed on Dec. 11, 2003.

(51) Int. Cl.
*A61F 5/44* (2006.01)
(52) U.S. Cl. .............. 604/345; 604/332; 604/338; 604/337; 604/342
(58) Field of Classification Search .............. 604/332, 604/337, 338, 342, 345
See application file for complete search history.

(56) References Cited

U.S. PATENT DOCUMENTS

| 4,592,750 A | * | 6/1986 | Kay | 604/337 |
|---|---|---|---|---|
| 4,681,574 A | | 7/1987 | Eastman | 604/344 |
| 5,626,570 A | | 5/1997 | Gallo | 604/345 |
| 5,865,820 A | | 2/1999 | Myello | 604/345 |
| 6,328,721 B1 | * | 12/2001 | Prohaska | 604/338 |

* cited by examiner

*Primary Examiner*—Jacqueline F. Stephens
(74) *Attorney, Agent, or Firm*—Goldstein Law Offices P.C.

(57) ABSTRACT

An ostomy appliance belt for supporting and concealing an ostomy pouch as well as the stoma area of the user's abdomen. The belt is made from a waterproof lightweight elastic material and completely encircles the user's waist without interfering with the attachment of the ostomy appliance to the abdomen. A flexible pocket retainer extends between the ends of the belt to support and contain the ostomy pouch in a retainer cup housed therein. The retainer cup is affixed to the user's body by a sealing barrier attached to the outer surface of the cup. The pocket retainer includes a one-way release valve that helps secure the pocket retainer to the user's body. A storage compartment is housed on the exterior side of the pocket retainer for storing personal items therein.

1 Claim, 2 Drawing Sheets

RECREATIONAL BELT FOR SUPPORTING AND HOUSING AN OSTOMY APPLIANCE

CROSS REFERENCES AND RELATED SUBJECT MATTER

This application is a continuation of provisional patent application Ser. No. 60/528,945, filed in the United States Patent Office on Dec. 11, 2003.

BACKGROUND OF THE INVENTION

The invention relates to a medical garment, and more particularly, to an improved support belt for securely supporting and housing an ostomy appliance. The belt is designed to support an ostomy collection bag or pouch in a secure position suctioned to the user's abdomen by a sealing barrier without interfering with the functions of the ostomy appliance. The collection pouch is held completely covered in the waterproof retaining cup and out of sight. The waterproof retaining cup and flexible lightweight belt allow users to engage in everyday activities including water sports with complete confidence and comfort.

As used herein the term "ostomy" is intended to cover all types of procedures such an ileostomy and colostomy wherein a passageway is provided through the skin and a portion of the intestine or stoma is surgically connected thereto for discharge of fecal matter or for other purposes. In its broadest scope the invention is suitable for use in conjunction with any surgical procedure requiring support of a bag, pouch or other container or apparatus for connection to a body entry device for receiving or discharging substance.

Prior to the development of appliances that attach to the exterior abdominal wall and collect waste material draining from the user's intestine in solid containers, the common practice was to position a moisture proof, sometimes expandable, material against the abdominal wall to form a cavity between the abdominal wall and the material for collecting discharged waste matter. The problems of personal hygiene, discomfort and activity limitations when using this type of device are readily apparent. The psychological effects on the user were also severe. Examples of such appliances appear in the prior art, for example, in U.S. Pat. No. 4,681,574 issued in the name of Eastman.

An example of an ostomy appliance belt was disclosed in U.S. Pat. No. 5,626,570, in the name of Gallo. Another example of an ostomy appliance was disclosed in U.S. Pat. No. 5,865,82, in the name of Myello. The Myello '820 patent disclosed a water resistant protection sealing apparatus for an ileostomy or urostomy appliance.

While these units may be suitable for the particular purpose employed, or for general use, they would not be as suitable for the purposes of the present invention as disclosed hereafter.

SUMMARY OF THE INVENTION

It is an object of the invention to produce an ostomy appliance that fits securely to the user's body while still being comfortable. Accordingly, this invention is a flexible and lightweight elastic belt attached to a retaining cup that suctions to hold the ostomy pouch securely to the user's body.

It is another object of the invention to produce an ostomy appliance that can be used during aquatic activities. Accordingly, this invention utilizes a waterproof elastic belt that houses an ostomy pouch securely against the user's abdomen by a one-way release valve and sealing barrier.

It is yet another objective of the invention to provide users with increased confidence and security to interact with others in public places. Accordingly, the invention's one-way release valve, sealing barrier, adjustable elastic belt, and retaining cup secure and contain the ostomy pouch tightly to the user.

It is yet another object of the invention to provide a storage pouch for housing personal items. Accordingly, a waterproof storage compartment is built into the exterior surface of the nylon retainer for housing items therein.

This invention features an appliance for accomplishing positive support and concealment of an ostomy pouch, which provides increased comfort, security and confidence to the user. The belt can be constructed from flexible, waterproof, and lightweight material that is important for personal hygiene. The belt can be adjusted around the body of the user by a hook and loop fastener for maximum support and comfort. The flexible pocket retainer includes a retaining cup attached therein by a hook and loop fastener, which together house and conceal the ostomy pouch. The pocket retainer and retaining cup are securely fastened to the body of the user around the ostomy pouch by a sealing barrier that suctions to the user's body with the help of the one-way release valve working as a suction. The invention further features a storage compartment within the retainer for storing person items therein.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
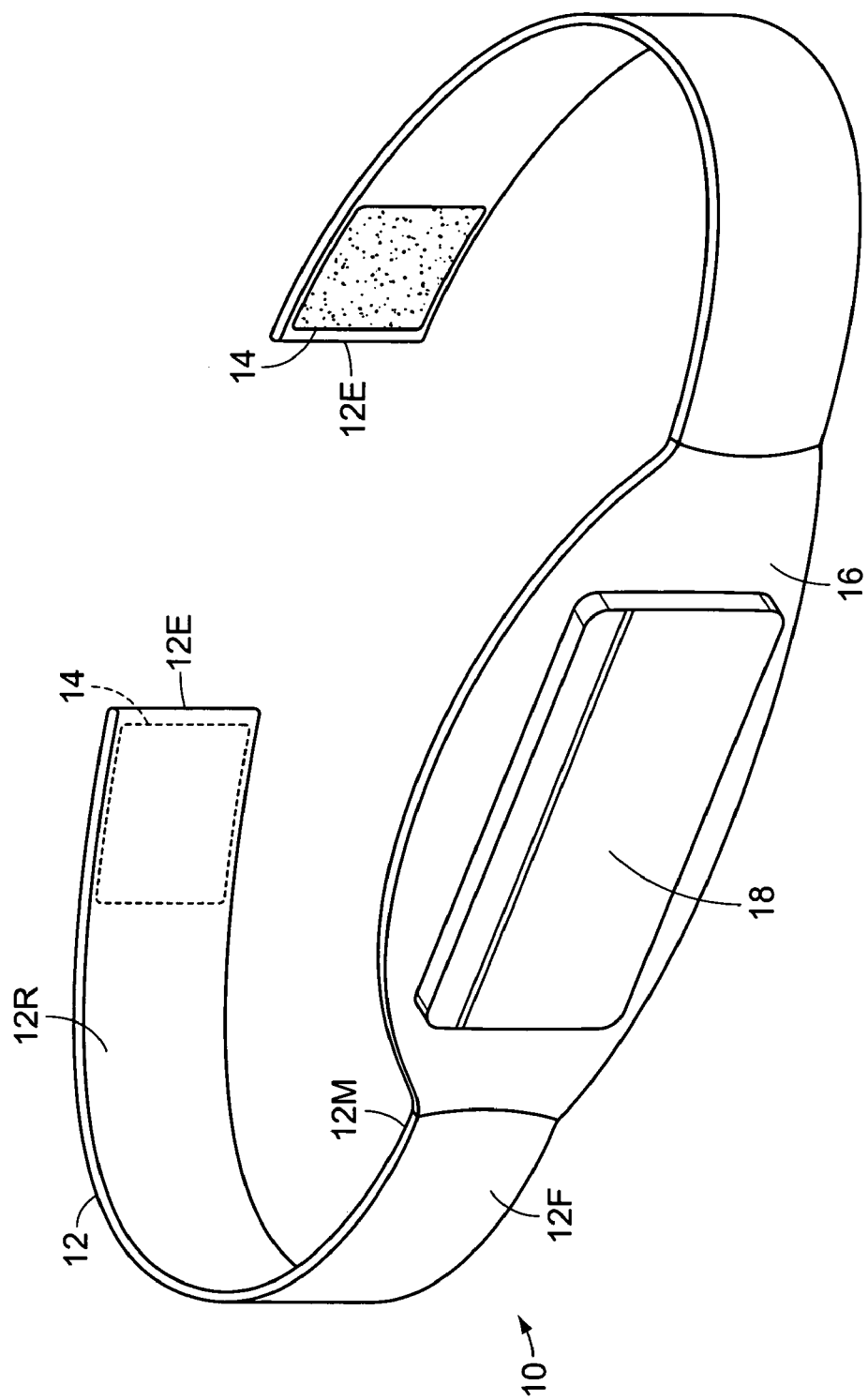
FIG. 1 is a perspective view of the ostomy appliance belt according to the present invention.

FIG. 1 illustrates an ostomy appliance belt 10, which includes an elastic belt 12 having a pair of belt ends 12E, and a belt middle 12M. Hook and loop fastener material 14 is located at each end of the belt's ends 12E. The belt 12 is securely fastened to the user by joining the belt ends 12E and adjusting the hook and loop fastener 14 for comfort and security. The elastic belt 12 is significantly wider at the belt middle 12M such that a flexible pocket retainer 16 is located at the belt middle 12M and divides the belt 12 in two. The belt 12 is made of waterproof and elastic material and has a front 12F and a rear 12R and a flexible pocket retainer 16, houses an exterior storage compartment 18 at the belt front 12F, for holding personal items therein.

Figure 2:
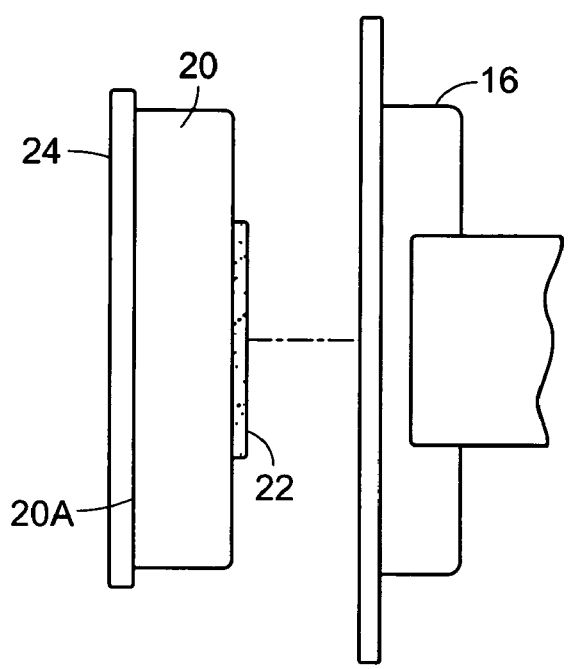
FIG. 2 is a side view showing the relationship between the retainer, the retaining cup and the sealing barrier.

FIG. 2 illustrates the interconnection of the pocket retainer 16 with a retaining cup 20, by a hook and loop fastener 22. The retaining cup 20 has an outer surface 20A, fully opposite from the hook and loop fastener 22 thereon. A sealing barrier ring 24 is affixed to the outer surface 20A of retaining cup 20. The sealing barrier ring 24 is large enough to encircle the ostomy pouch and stoma region. Accordingly, when the elastic belt 12 is properly secured around the user by joining the ends thereof using the hook and loop fastener material, the sealing barrier ring 24 engages the user's body around the ostomy pouch and helps hold the pocket retainer 16 securely and comfortably against the user's body, supporting and concealing the ostomy pouch as well as the stoma area of the user's abdomen.

Figure 3:
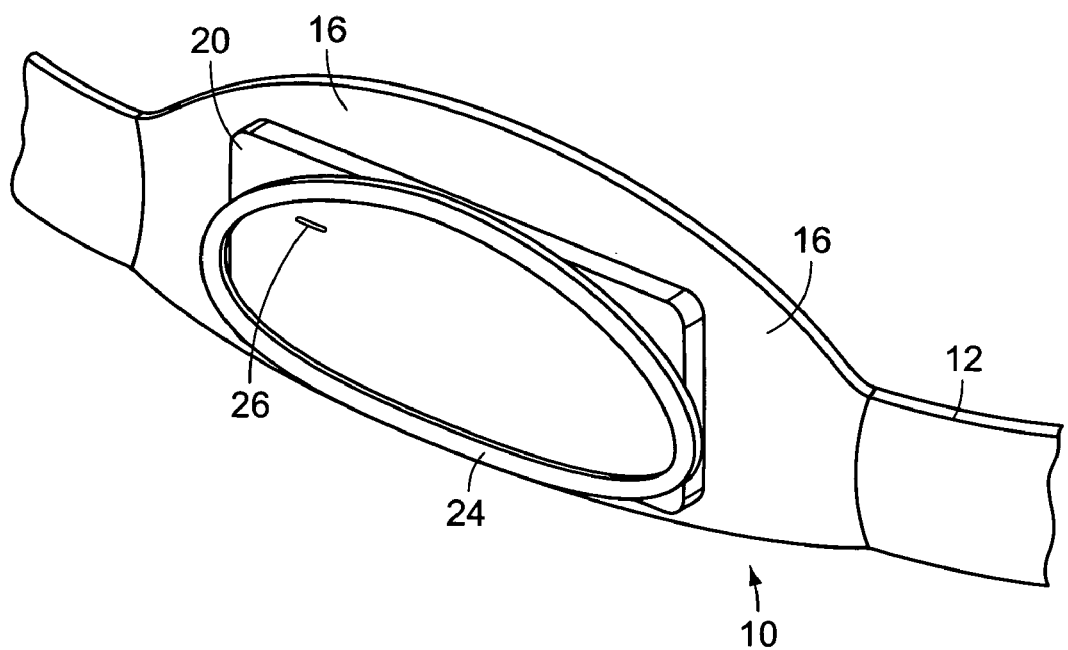
FIG. 3 is a back view of ostomy appliance belt detailing the one-way release valve, which is housed inside of the retaining cup.

FIG. 3 provides a back view of the pocket retainer 16 and shows its relationship with the retainer cup 20 and the sealing barrier ring 24. A one-way release valve 26 is shown within the retaining cup 20 and allows air to be evacuated from the cavity created by the retaining cup 20, the sealing barrier 24, and the user's body, but prevents water infiltration therein. The one-way release valve may be as simple as a slit with flaps configured to open in one direction to release air from the retaining cup 20, but then resisting opening in a manner that allows air to enter the retaining cup 20. Accordingly, as air escapes through the release valve 26 suction is created that holds the retainer cup 20 securely and comfortably to the user's body and helps maintain a waterproof seal at the sealing barrier ring 24, so that the user can safely swim with the belt 10 installed.

In conclusion, herein is presented a waterproof and comfortable ostomy appliance belt. The invention is illustrated by example in the drawing figures, and throughout the written description. It should be understood that numerous variations are possible, while adhering to the inventive concept. Such variations are contemplated as being a part of the present invention.

What is claimed is:

1. An ostomy appliance belt for use by a user having an ostomy pouch and stoma area, for supporting and concealing the ostomy pouch and stoma area, comprising:

a flexible belt made of flexible and waterproof material, having a pair of belt ends and a belt middle, a front and rear, a storage pocket at the front, hook and loop fastener material located at each of the belt ends for selectively securing the belt around the user and selectively detaching the belt therefrom, and a flexible pocket retainer located at the belt middle; and a retainer cup attached to the flexible pocket retainer at the belt rear and having a sealing barrier ring for adhering to the user around the stoma reason for containing the ostomy pouch within the retainer cup, the retainer cup has a one-way release valve to allow air to escape the retainer cup to facilitate a seal at the sealing barrier ring between the retainer cup and user.

* * * * *